US006649185B2

(12) United States Patent
Solanki

(10) Patent No.: US 6,649,185 B2
(45) Date of Patent: Nov. 18, 2003

(54) HERBAL FORMULATION

(75) Inventor: Ranjitsinh Solanki, Gujarat (IN)

(73) Assignee: Sahajanand Biotech Private Limited, Gujarat (IN)

( * ) Notice: Subject to any disclaimer, the term of this patent is extended or adjusted under 35 U.S.C. 154(b) by 0 days.

(21) Appl. No.: 10/257,092

(22) PCT Filed: Jul. 10, 2002

(86) PCT No.: PCT/IB02/02701

§ 371 (c)(1),
(2), (4) Date: Oct. 8, 2002

(87) PCT Pub. No.: WO03/006034

PCT Pub. Date: Jan. 23, 2003

(65) Prior Publication Data

US 2003/0152585 A1 Aug. 14, 2003

(30) Foreign Application Priority Data

Jul. 11, 2001 (GB) .............................................. 0116949

(51) Int. Cl.⁷ .......................... A61K 9/00; A61K 47/00; A61K 35/78

(52) U.S. Cl. ........................ 424/439; 424/400; 424/725
(58) Field of Search ................................. 424/400, 439, 424/725

(56) References Cited

U.S. PATENT DOCUMENTS 5,693,327 A * 12/1997 Shah ........................ 424/195.1
6,080,401 A * 6/2000 Reddy et al. ............... 424/93.3
6,264,995 B1 * 7/2001 Newmark et al. .......... 424/725

* cited by examiner

Primary Examiner—Thurman K. Page
Assistant Examiner—S. Oh
(74) Attorney, Agent, or Firm—Volpe and Koenig, P.C.

(57) ABSTRACT

A pharmaceutical or medicinal preparation which comprises a mixture of the following seven herbs: *Tinospora cordifolia, Aloa vera (Aloa barbedensis), Curcuma longa, Withania somnifera, Achyranthus aspera, Ocimum sanctum* and *Picorrhiza kurroa*, or a mixture of the active ingredients that have been extracted from those herbs or chemically synthesised. The herbal formulation of the invention is effective for the treatment of cancer, in particular haematological malignancies.

18 Claims, No Drawings

HERBAL FORMULATION

TECHNICAL FIELD

This invention relates to a new herbal formulation which has been found to be effective for the treatment of cancer. More particularly, the formulation can be used to treat haematological malignancies.

The conventional treatment of cancer comprises surgery, chemotherapy and/or radiotherapy. The drugs given during chemotherapy are of necessity very powerful and, in consequence, can have serious and undesirable side-effects. There is therefore a need for improved pharmaceutical or medicinal preparations for use in the treatment of cancer. It is the object of this invention to provide such a product.

According to this invention there is provided a pharmaceutical or medicinal preparation which comprises a mixture of the following seven herbs: *Tinospora cordifolia, Aloe vera (Aloe barbedensis), Curcuma longa, Withania somnifera, Achyranthus aspera, Ocimum sanctum* and *Picorrhiza kurroa,* or a mixture of the active ingredients that have been extracted from those herbs or chemically synthesized. This product has been found by the inventors to be particularly effective for the treatment of all acute leukaemias, including acute lymphoblastic leukaemias (L1–L3) and cute myeloblastic leukaemias (M1–M7). It also increases platelet count in cases of thrombocytopenia in leukaemias, ITP, TTP, etc and, furthermore, it increases haemoglobin concentration in anaemic patients. The preparation is preferably formulated for administration to patients as a liquid or syrup, but could also be administered as a capsule or tablet.

The ingredients for a typical herbal formulation according to this invention are set out in Table 1. It should be appreciated that the proportions of the individual herbs may be varied and the figure quoted in Table 1 are by way of illustration only. In particular, the proportions of one or more of the components may be varied in order to optimize the pharmacological effects produced by the formulation to suit the specific needs of patients being treated.

It is an important feature of the product of the present invention that it contains a mixture of herbs, or extracts from herbs, rather than being based on a single herb. A synergistic effect has been noticed between various ingredients. The synergistic activity is surprising and unexpected. The activities of similar herbs are combined to optimize and enhance the pharmacological effects without increasing the adverse toxic reactions (which becomes a distinct possibility if the herbs are used singly in a concentration of 100%). The advantage of a multi-drug regimen also lies in the fact that the possibility of development of drug resistance is minimized.

Preliminary clinical trials of the product of this invention have produced definite clinical evidence of improvement in the condition of patients suffering from acute leukaemia. These improvements include:

i) reduction in the number of leukaemic blast cells in the peripheral blood cells as well as the bone marrow; and
ii) improvement in the relevant biochemical parameters; and more subjectively:
  i) sense of well being,
  ii) improvement in appetite, and
  iii) increased vigour and enthusiasm is daily activities.

The formulation of this invention is itself effective for the treatment of cancer. It may also be used s an adjuvant to conventional modes of anticancer therapy, namely radiotherapy and/or chemotherapy. The formulation may be presented as a dietary supplement for patients diagnosed as having any type of cancer. It may also be used to create a sense of general well being and to increase the vitality in patients diagnosed as having any type of cancer; to increase the appetite, restore health and increase the lifespan of patients diagnosed as having any type of cancer, to improve the ambulatory capacity in patients diagnosed as having any type of cancer; to activate the nervous system, prevent degenerative changes, stimulate regeneration and improve the psychological status in patients diagnosed as having any type of cancer; and to stimulate metabolism, accelerate anabolism, promote catabolism thereby flushing the body of toxic metabolites and reducing the side effects of chemotherapy and radiotherapy. The hepatic clearance of substances like iron and ferritin in cases of thalassemia is also improved, thereby reducing the iron overload in such ideas.

The manufacture of a product according to the present invention will now be illustrated by the following example. However, it will be appreciated that the active ingredients may be chemically synthesised as an alternative to being extracted from the natural herbs.

EXAMPLES

Method of Extraction

Each of the herbal components of the formulation were de-seeded (wherever required), ground finely to powder form and then submitted individually to conventional solvent extraction methods.

By way of illustration only, the extraction can be performed by using volatile freon gas. This process has the advantage of being fast and also has the ability to preserve the active chemicals (alkaloids, non-alkaloids, electrolytes, minerals, etc.) in their natural form (as it does not involve heating and denaturation at any stage of the process). Freon, being a highly volatile compound with its boiling point at −21° C., evaporates totally after extraction yielding an ultrapure concentrate of the chemicals. The chemicals are thereafter diluted appropriately and mixed in the proportions mentioned in Table 1.

Preliminary Clinical Data

Case 1

The patient was a five year old male diagnosed (at the Tata Memorial Centre Hospital in Mumbai) as having common acute lymphoblastic leukaemia on Aug. 20, 1999. A course of chemotherapy and radiotherapy (MCP-8HI Protocol) was started on the same date and completed on Feb. 8, 2000. The patient suffered the known side effects of radiotherapy and chemotherapy, including loss of weight, no appetite and fatigue. The patient's bone marrow aspiration report suggested only a partial response to the treatment and a relapse of the leukaemia. In consequence, the patient was considered to be terminally ill with a very short life expectancy.

On Feb.12, 2000, the patient began taking the herbal formulation of the present invention. The formulation as defined in Table 1 was administered to the patient in the form of a liquid at a dosage of 3 mg/kg body weight per day. After taking the formulation for a period of one month, the condition of the patient was found to be improved. He had a good appetite, had gained weight and was cheerful.

The results of a pathology examination suggested a significant improvement in the patient's haematological profile. The haematology report found the patient to be in remission and no abnormal cells or blasts were seen. A bone marrow aspiration performed at the Tata Memorial Centre suggested a normal profile.

These findings suggest that the herbal formulation of the present invention is very effective in treating even terminal cases of acute lymphoblastic leukaemia. Furthermore, it appears to produce no adverse side effects, targets only malignant cells and produces an improved immunomodulatory effect.

Case 2

A 78 year old patient was diagnosed as having chronic lymphocytic leukaemia at a cancer hospital in Ahmedabad in February, 2002. Thereafter, he received chemotherapy. The herbal therapy of the present invention was instituted as an adjuvant to chemotherapy in this case. After two months of herbal therapy, there was an improvement in the haematological profile of the patient as seen in the increase of haemoglobin and platelet counts. The patient also had improved appetite, ambulation and improved psychological status. He could carry out his routine activities on his own. This proves that the herbal therapy of the present invention is effective as an adjuvant to conventional therapy and is useful in reducing the toxic effects of chemotherapy, and also in creating a sense of general well being in the patient. The primary parameters which form the diagnostic hallmarks of chronic lymphocytic leukemia could not be assessed in this case due to concomitant chemotherapy.

TABLE 1

Polyherbal formulation for Haematological Malignancies
Description of Ingredients

| Sr. No. | Latin Binomial | Common Names | Distribution | Parts used | Quantity | Adverse Reactions |
|---|---|---|---|---|---|---|
| 1 | Tinospora cordifolia | Tinospora, Guduchi, Amrita | Throughout India in forests | Stem | 35–45% preferably 40% | None |
| 2 | Aloe Vera (Aloe Barbedensis) | Indian Aloe, Kumari | More in the drier parts of India | Leaf juice, elio | 17–23% preferably 20% | None |
| 3. | Curcuma longa | Turmeric, Haldi, Haridra | Cultivated throughout India | Rhizomes (dried as well as raw) | 8–12% preferably 10% | None |
| 4. | Withania Somnifera | Ashwagandha | All parts of India | Roots, leaves | 8–12% preferably 10% | None |
| 5. | Achyranthus aspera | Prickly Chaff, Apamarg | Throughout India along roadsides and waste places | Whole plant | 3–8% preferably 5% | None |
| 6. | Ocimum Sanctum | Holy Basil, Tulsi | Cultivated throughout Indiag | Leaves | 3–8% preferably 5% | None |
| 7. | Picorthiza Kurroa | Kadu | Cultivated throughout India | Leaves | 8–12% preferably 10% | None |

What is claimed is:

1. A pharmaceutical or medicinal preparation comprising a mixture of herbs within the following ranges:

| | |
|---|---|
| Tinospora cardifolia | 35–45% |
| Aloe vera (Aloe barbedensis) | 17–23% |
| Curcuma longa | 8–12% |
| Withania somnifera | 8–12% |
| Achyranthus aspera | 3–8% |
| Ocimum Sanctum | 3–8% |
| Picorhiza kurroa | 8–12%. |

2. A pharmaceutical or medicinal preparation as claimed in claim 1, for use in the treatment of cancer.

3. A pharmaceutical or medicinal preparation as claimed in claim 1, for use in the treatment of haematological malignancies.

4. A pharmaceutical or medicinal preparation as claimed in claim 1, for use in the treatment of leukaemias.

5. A pharmaceutical or medicinal preparation as claimed in claim 1, for use in the treatment of anaemia.

6. A pharmaceutical or medicinal preparation as claimed in claim 1, for use as an adjuvant to radiotherapy.

7. A pharmaceutical or medicinal preparation as claimed in claim 1, wherein the amount of herbs is under:

| | |
|---|---|
| Tinospora cardifolia | 40% |
| Aloe vera (Aloe barbedensis) | 20% |
| Curcuma longa | 10% |
| Withania somnifera | 10% |
| Achyranthus aspera | 5% |
| Ocimum Sanctum | 5% |
| Picorrhiza kurroa | 10%. |

8. A dietary supplement for patients diagnosed as having any type of cancer, which includes a pharmaceutical or medicinal preparation as claimed in claim 1.

9. A pharmaceutical or medicinal preparation as claimed in claim 1, for use as an adjuvant to chemotherapy.

10. A pharmaceutical or medicinal mixture of active ingredients that have been extracted from herbs, the mixture comprising herbal active ingredients within the following ranges:

| | |
|---|---|
| Tinospora cardifolia | 35–45% |
| Aloe vera (Aloe barbedensis) | 17–23% |
| Curcuma longa | 8–12% |
| Withania somnifera | 8–12% |
| Achyranthus aspera | 3–8% |

-continued

| | |
|---|---|
| *Ocimum Sanctum* | 3–8% |
| *Picorrhiza kurroa* | 8–12%. |

11. A pharmaceutical or medicinal mixture as claimed in claim 10, for use in the treatment of cancer.

12. A pharmaceutical or medicinal mixture as claimed in claim 10, for use in the treatment of haematological malignancies.

13. A pharmaceutical or medicinal mixture as claimed in claim 10, for use in the treatment of leukaemias.

14. A pharmaceutical or medicinal mixture as claimed in claim 10, for use in the treatment of anaemia.

15. A pharmaceutical or medicinal mixture as claimed in claim 10, for use as an adjuvant to radiotherapy.

16. A pharmaceutical or medicinal mixture as claimed in claim 10, for use as an adjuvant to chemotherapy.

17. A pharmaceutical or medicinal mixture as claimed in claim 10, wherein the amount of active ingredients extracted from the following herbs is under:

| | |
|---|---|
| *Tinospora cardifolia* | 40% |
| Aloe vera (Aloe barbedensis) | 20% |
| *Curcuma longa* | 10% |
| *Withania somnifera* | 10% |
| *Achyranthus aspera* | 5% |
| *Ocimum Sanctum* | 5% |
| *Picorrhiza kurroa* | 10%. |

18. A dietary supplement for patients diagnosed as having any type of cancer, which includes a pharmaceutical or medicinal mixture as claimed in claim 10.

\* \* \* \* \*